(12) United States Patent
von Hatten et al.

(10) Patent No.: US 9,982,250 B2
(45) Date of Patent: May 29, 2018

(54) REVERSIBLE SURFACE FUNCTIONALIZATION

(71) Applicant: Illumina Cambridge Limited, Nr Saffron Walden, Essex (GB)

(72) Inventors: Xavier von Hatten, Nr Saffron Walden (GB); Wayne N. George, Nr Saffron Walden (GB); Alexandre Richez, Nr Saffron Walden (GB); Anne-Cecile Dingwall, Nr Saffron Walden (GB); Andrew A. Brown, Nr Saffron Walden (GB)

(73) Assignee: Illumina Cambridge Limited, Essex (GB)

( * ) Notice: Subject to any disclaimer, the term of this patent is extended or adjusted under 35 U.S.C. 154(b) by 0 days. days.

(21) Appl. No.: 14/831,062

(22) Filed: Aug. 20, 2015

(65) Prior Publication Data

US 2016/0053252 A1 Feb. 25, 2016

Related U.S. Application Data

(60) Provisional application No. 62/040,323, filed on Aug. 21, 2014.

(51) Int. Cl.
*C12Q 1/68* (2018.01)
*C12N 11/10* (2006.01)
*G01N 33/543* (2006.01)
*G01N 33/551* (2006.01)

(52) U.S. Cl.
CPC ............ *C12N 11/10* (2013.01); *C12Q 1/6834* (2013.01); *C12Q 1/6869* (2013.01); *G01N 33/543* (2013.01); *G01N 33/54353* (2013.01); *G01N 33/551* (2013.01)

(58) Field of Classification Search
None
See application file for complete search history.

(56) References Cited

U.S. PATENT DOCUMENTS 4,307,245 A * 12/1981 Hu ..................... G01N 33/531
436/823
5,130,238 A 7/1992 Malek et al.
5,429,807 A 7/1995 Matson et al.
(Continued)

FOREIGN PATENT DOCUMENTS

EP 742 287 11/1996
EP 799 897 10/1997
(Continued)

OTHER PUBLICATIONS

Duan et al "Regenerative electronic biosensors using supramolecular approaches" ACS Nano, 7: 4014-4021.*
(Continued)

*Primary Examiner* — Betty J Forman
(74) *Attorney, Agent, or Firm* — Knobbe Martens Olson & Bear LLP

(57) ABSTRACT

Some embodiments described herein relate to a substrate comprising a silane functionalized surface for reversibly immobilizing a biological molecule of interest, such as oligonucleotides, polynucleotides, or protein. Methods for immobilizing the biological molecule and the use in DNA sequencing and other diagnostic applications are also disclosed.

19 Claims, 3 Drawing Sheets

(56) References Cited

U.S. PATENT DOCUMENTS

| | | | |
|---|---|---|---|
| 5,436,327 | A | 7/1995 | Southern et al. |
| 5,455,166 | A | 10/1995 | Walker |
| 5,561,071 | A | 10/1996 | Hollenberg et al. |
| 5,583,211 | A | 12/1996 | Coassin et al. |
| 5,599,675 | A | 2/1997 | Brenner |
| 5,641,658 | A | 6/1997 | Adams et al. |
| 5,658,734 | A | 8/1997 | Brock et al. |
| 5,750,341 | A | 5/1998 | Macevicz |
| 5,837,858 | A | 11/1998 | Brennan |
| 5,874,219 | A | 2/1999 | Rava et al. |
| 5,919,523 | A | 7/1999 | Sundberg et al. |
| 6,136,269 | A | 10/2000 | Winkler et al. |
| 6,210,891 | B1 | 4/2001 | Nyren et al. |
| 6,214,587 | B1 | 4/2001 | Dattagupta et al. |
| 6,258,568 | B1 | 7/2001 | Nyren |
| 6,274,320 | B1 | 8/2001 | Rothberg et al. |
| 6,287,768 | B1 | 9/2001 | Chenchik et al. |
| 6,287,776 | B1 | 9/2001 | Hefti |
| 6,288,220 | B1 | 9/2001 | Kambara et al. |
| 6,291,193 | B1 | 9/2001 | Khodadoust |
| 6,297,006 | B1 | 10/2001 | Drmanac et al. |
| 6,346,413 | B1 | 2/2002 | Fodor et al. |
| 6,355,431 | B1 | 3/2002 | Chee et al. |
| 6,416,949 | B1 | 7/2002 | Dower et al. |
| 6,482,591 | B2 | 11/2002 | Lockhart et al. |
| 6,514,751 | B2 | 2/2003 | Johann et al. |
| 6,524,793 | B1 | 2/2003 | Chandler et al. |
| 6,610,482 | B1 | 8/2003 | Fodor et al. |
| 6,890,741 | B2 | 5/2005 | Fan et al. |
| 6,913,884 | B2 | 7/2005 | Stuelpnagel et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,244,559 | B2 | 7/2007 | Rothberg et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,582,420 | B2 | 9/2009 | Oliphant et al. |
| 7,595,883 | B1 | 9/2009 | El Gamal et al. |
| 7,622,294 | B2 | 11/2009 | Walt et al. |
| 8,778,848 | B2 | 7/2014 | Lin et al. |
| 8,778,849 | B2 | 7/2014 | Bowen et al. |
| 9,012,022 | B2 | 4/2015 | George et al. |
| 2002/0055100 | A1 | 5/2002 | Kawashima et al. |
| 2002/0102578 | A1 | 8/2002 | Dickinson et al. |
| 2002/0197694 | A1* | 12/2002 | Shao ............... C07K 16/00 435/188.5 |
| 2004/0002090 | A1 | 1/2004 | Mayer et al. |
| 2004/0096853 | A1 | 5/2004 | Mayer |
| 2005/0053980 | A1 | 3/2005 | Gunderson et al. |
| 2005/0064460 | A1 | 3/2005 | Holliger et al. |
| 2005/0130173 | A1 | 6/2005 | Leamon et al. |
| 2005/0181440 | A1 | 8/2005 | Chee et al. |
| 2005/0191698 | A1 | 9/2005 | Chee et al. |
| 2007/0099208 | A1 | 5/2007 | Drmanac et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2009/0026082 | A1 | 1/2009 | Rothberg et al. |
| 2009/0127589 | A1 | 5/2009 | Rothberg et al. |
| 2009/0186349 | A1 | 7/2009 | Gunderson et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2011/0172118 | A1 | 7/2011 | Kain et al. |
| 2012/0072118 | A1* | 3/2012 | Mann ............... G01N 33/50 702/19 |
| 2012/0220518 | A1* | 8/2012 | von Recum ......... A61K 9/0024 514/2.3 |
| 2012/0270305 | A1 | 10/2012 | Reed et al. |
| 2014/0191186 | A1 | 7/2014 | Reed et al. |
| 2014/0243224 | A1 | 8/2014 | Barnard et al. |
| 2015/0005447 | A1 | 1/2015 | Berti et al. |

FOREIGN PATENT DOCUMENTS

| | | |
|---|---|---|
| EP | 2463386 A2 | 6/2012 |
| WO | WO 89/10977 A1 | 11/1989 |
| WO | WO 91/06678 | 5/1991 |
| WO | WO 93/17126 | 9/1993 |
| WO | WO 95/11995 | 5/1995 |
| WO | WO 95/35505 | 12/1995 |
| WO | WO 00/63437 | 10/2000 |
| WO | WO 2004/018497 | 3/2004 |
| WO | WO 2005/010145 | 2/2005 |
| WO | WO 2007/123744 | 11/2007 |
| WO | WO 2012/058096 A1 | 5/2012 |
| WO | WO 2012/093162 A1 | 7/2012 |

OTHER PUBLICATIONS

ChemSpider.com, "adamantane", printed Jan. 19, 2017.*
International Search Report and Written Opinion for Application No. PCT/EP2015/069128, dated Dec. 4, 2015.
Szarpak-Jankowksa, Anna, et al., Cyclodextrin-Modified Zeolites: Host-Guest Surface Chemistry for the Construction of Multifunctional Nanocontainers, Chem. Eur. J. 2013, 19: 14925-14930.
Zhang Yanrong, et al, Fabrication of Reversible Poly(dimethylsiloxane) Surfaces via Host-Guest Chemistry and Their Repeated Utilization in Cardiac Biomarker Analysis, Anal. Chem. 2011, 83: 9651-9659.
Li, H.B., et al., Preparation and Application of a Novel Type of Calix[6]crown Coated Capillary for Open-tubular Capillary Electrochromatography, Chromatographia 2002, 55, May (No. 9/10): 591-594.
Bentley et al., Nature 456:53-59 (2008).
Black, et al in Chem. Soc. Rev., 2014, 43, pp. 1861-1872.
Dressman et al., Proc. Natl. Acad. Sci. USA 100:8817-8822 (2003).
Liu et al., Macromolecular Chemistry and Physics, 2007, 208(2), pp. 224-232.
Nitschke in Acc. Chem. Res., 2007, 40 (2), pp. 103-112.
Seto, et al in J. Am. Chem. Soc., 1993, 115 (4), pp. 1321-1329.
Schenning, et al in Chem. Commun. 2005, 14; (26):3245-58.
Stoddart Chem. Soc. Rev., 2012, 41, pp. 2003-2024.
Stoddart Chem. Soc. Rev. 2007, 36(11), pp. 1705-1723.
Wickstrom et al, J. Chem. Theory Comput. 2013, 9, 3136-3150.
Wilson, et al in Chem. Soc. Rev., 2014, 43, pp. 1948-1962.
Bains et al., (1988) A novel method for nucleic acid sequence determination. Journal of Theoretical Biology, 135(3):303-307.
Dean et al., (2002) Comprehensive human genome amplification using multiple displacement amplification. Proc Natl. Acad. Sci. USA, 99(8):5261-5266.
Drmanac et al., (1998) Accurate sequencing by hybridization for DNA diagnostics and individual genomics. Nature Biotechnology, 16:54-58.
Fodor et al., (1991) Light-directed, spatially addressable parallel chemical synthesis. Science, 251(4995):767-773.
Korlach et al., (2008) Selective aluminum passivation for targeted immobilization of single DNA polymerase molecules in zero-mode waveguide nanostructures. Proc. Natl. Acad. Sci. USA, 105(4):1176-1181.
Lage et al., (2003) Whole genome analysis of genetic alterations in small DNA samples using hyperbranched strand displacement amplification and array-CGH. Genome Research, 13:294-307.
Levene et al., (2003) Zero-mode waveguides for single-molecule analysis at high concentrations. Science, 299(5607):682-686.
Lizardi et al., (1998) Mutation detection and single-molecule counting using isothermal rolling-circle amplification. Nature Genetics, 19:225-232.
Lundquist et al., (2008) Parallel confocal detection of single molecules in real time. Optics Letters, 33(9):1026-1028.
Ronaghi, et al., (1996) Real-time DNA sequencing using detection of pyrophosphate release. Analytical Biochemistry, 242(1):84-89.
Ronaghi et al., (1998) A sequencing method based on real-time pyrophosphate. Science, 281(5375):363-365.
Ronaghi (2001) Pyrosequencing sheds light on DNA sequencing. Genome Research, 11:3-11.

(56) References Cited

OTHER PUBLICATIONS

Shendure et al., (2005) Accurate multiplex polony sequencing of an evolved bacterial genome. *Science*, 309:1728-1732.

Walker et al., (1992) Strand displacement amplification—an isothermal, in vitro DNA amplification technique. *Nucleic Acids Research*, 20(7):1691-1696.

Walker et al., (1995) A chemiluminescent DNA probe test based on strand displacement amplification. In Danny L. Wiedbrauk and Daniel H. Farkas (Eds.), *Molecular Methods for Virus Detection* (pp. 329-349). San Diego: Academic Press, Inc.

\* cited by examiner

SEQUENCE LISTING

<160> NUMBER OF SEQ ID NOS: 4

<210> SEQ ID NO 1
<211> LENGTH: 29
<212> TYPE: DNA

```
<213> ORGANISM: Artificial Sequence
<220> FEATURE:
<223> OTHER INFORMATION: Primer

<400> SEQUENCE: 1
aatgatacgg cgaccaccga gauctacac                                      29

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
caagcagaag acggcatacg agat                                           24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aatgatacgg cgaccaccga                                                20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
caagcagaag acggcatacg a                                              21
```

REVERSIBLE SURFACE FUNCTIONALIZATION

INCORPORATION BY REFERENCE TO ANY PRIORITY APPLICATIONS

The present application claims the benefit of priority to U.S. Provisional Patent Application No. 62/040,323, filed on Aug. 21, 2014, which is hereby expressly incorporated by reference in its entirety.

REFERENCE TO SEQUENCE LISTING

The present application includes a sequence listing in Electronic format. The Sequence Listing is provided as a file entitled ILLINC.274A.txt created Nov. 4, 2015 which is approximately 5 kb in size. The information in the electronic format of the sequence listing is incorporated herein by reference in its entirety.

FIELD

In general, the present application relates to the fields of chemistry, biology and material science. More specifically, the present application relates to a substrate comprising a silane functionalized surface for reversibly immobilizing a biological molecule of interest. Methods for immobilizing a biological molecule and the use in DNA sequencing and other diagnostic applications are also disclosed.

BACKGROUND

Polymer or hydrogel-coated substrates are used in many technological applications. For example, polymer or hydrogel coated substrates are used for the preparation and/or analysis of biological molecules. Molecular analyses, such as certain nucleic acid sequencing methods, utilize the attachment of nucleic acid strands to a polymer or hydrogel-coated surface of a substrate. The sequences of the attached nucleic acid strands can then be determined by a number of different methods that are well known in the art.

Sequencing-by-synthesis (SBS) typically exploits the attachment of template DNA strands to a polymer-coated flowcell surface. An exemplary procedure for preparing the glass surface of a flowcell for SBS comprises: (1) functionalization of the surface with a reactive silane by chemical vapor deposition (CVD); (2) covalently attaching a preformed polyamide polymer to the flow cell surface by a thermal reaction; and (3) attaching sequencing primers to a reactive moiety of the polymer using crosslinking chemistry. After the surface is prepared, DNA is attached to the primers on the surface, amplified to generate clusters which are then sequenced-by-synthesis to read individual bases in the sequence. Every step of the preparation of the flow cell surface or coating is amenable to being performed in solution using microfluidics and therefore can be performed on-board the instrument. The deposition of the polymer layer can also be performed by spin or spray coating. One typical exception is the CVD of functionalized silane, which is performed in a high temperature vacuum oven.

Although it is known that a strong base can be used to efficiently remove the silane layer, this method would create the need for a CVD oven in order to renew the flow cell. The current state-of-the art is that after the sequencing is performed, the flow cell is not reused for sequencing and is instead disposed. No efficient way of renewing the flow cell are commercially available. Therefore, it would be desirable to design a sequencing process where the flow cell can be regenerated or recycled to reduce the cost associated with SBS.

SUMMARY

The present application relates to new approaches to immobilize or anchor a biological molecule of interest, such as DNA on the flow cell surface using reversible interactions, such as non-covalent interactions. These approaches will enable multiple use of a flow cell and the entire process can be performed on-board an instrument using a separate reagent plate or a regular reagent plate with more reagents. For example, one approach uses host/guest or inclusion complexes chemistry to reversibly attach particular SBS primers onto a glass surface. The systems and methods exemplified herein for nucleic acids and other biological molecules can be extended to a variety of biological components such as cells, viruses, organelles or particles. For example, biological molecules on the surfaces of these biological components can be immobilized and manipulated to achieve several of the advantages set forth herein for biological molecules and to achieve other advantages a well. Similarly, the systems and methods set forth herein can be extended to non-biological molecules by replacing non-biological molecules for the biological molecules exemplified herein.

The recognition event between the functionalized surface and the complimentary functionalized polymer and/or self-assembled monolayer may take place through a variety of reversible attractive intermolecular interactions, being covalent or non-covalent. Other non-limiting examples for functionalized surface via reversible non-covalent interactions include van der Waals interactions (such as hydrogen bonding, e.g., molecular recognition of carboxylic acid), π-π interactions (such as π-stacking of aromatic compounds), metal-metal interactions, charge transfer interactions such as metal to ligand interactions (i.e. complexation of a metal ion into a ligand pocket).

Another approach involves the insertion of reversible covalent bonding between the substrate surface and the polymer. The reversible bond is stable during the sequencing but can be removed using a certain set of conditions. For example, the reversible bond may comprise a copper-imine complex between the functionalized silane layer and a layer of poly(N-(5-azidoacetamidylpentyl) acrylamide-co-acrylamide) (PAZAM). This copper imine ligation is reversible and could be cleaved under specific sets of circumstances. Other non-limiting examples of covalent reversible interactions include disulphide bond formations, boronic acid interactions with diols and/or other nucleophiles/Lewis bases, interactions between aldehyde with amine or alcohol (resulting the formation of imine or the formation of hemiacetal and acetal), hemiacetal and acetal can be further stabilized by interactions with a metal ions in diverse oxidation state, such as copper, iron, cobalt, nickel, zinc and cadmium.

Some embodiments described herein relate to a method for reversibly immobilizing a biological molecule to a surface of a substrate, comprising:
  providing a biological molecule covalently bonded to a host molecule, said host molecule comprises a hydrophilic portion and a hydrophobic portion;
  providing a substrate having a surface comprising functionalized silane covalently attached thereto, wherein the functionalized silane comprises a guest moiety that can form a host-guest complex with the host molecule;

contacting the biological molecule with the functionalized silane such that the biological molecule is immobilized to the surface through host-guest reversible interaction between the functionalized silane and the host molecule, the host-guest interaction being optionally non-covalent.

Some embodiments described herein relate to a substrate comprising a biological molecule immobilized to a surface of said substrate, wherein
said biological molecule is covalently bonded to a host molecule comprising a hydrophobic portion and a hydrophilic portion;
said surface of the substrate comprises functionalized silane covalently attached thereto, and said functionalized silane comprises a guest moiety that can form a host-guest complex with the host molecule;
wherein the biological molecule is immobilized through host-guest interaction between the functionalized silane and the host molecule, the host-guest interaction being optionally non-covalent.

In some embodiments, the guest moiety of the functionalized silane comprises a hydrophobic moiety. In some such embodiments, the host-guest interaction is a non-covalent interaction between the hydrophobic moiety of the functionalized silane and the hydrophobic portion of the host molecule.

In some embodiments, the biological molecule comprises an amino acid, peptide, nucleoside, nucleotide, oligonucleotide, polynucleotide, protein, sugar, polysaccharide or combinations thereof. In some such embodiments, the biological molecule comprises an oligonucleotide or polynucleotide. In some further embodiments, the oligonucleotide is a primer. In some such embodiments, the biological molecule is covalently bonded to the hydrophilic portion of the host molecule. In some such embodiments, the biological molecule is not a small organic molecule. In some embodiments, the biological molecule comprises oligonucleotide. In one embodiment, the biological molecule is a single strained DNA.

In some embodiments of the methods described herein, the method further comprises generating a clustered array of polynucleotides from the oligonucleotide. For example, the oligonucleotide can function as a primer for amplification of a template nucleic acid that hybridizes to the oligonucleotide.

In some embodiments, the host molecule is an optionally substituted cyclodextrin or derivative thereof. In some such embodiments, the host molecule is β-cyclodextrin. In some such embodiments, the host molecule is α-cyclodextrin. In some other such embodiments, the host molecule is γ-cyclodextrin. Other cyclodextrins with bigger ring sizes can also be used depending on the size of the hydrophobic guest moiety.

In some embodiments of the method described herein, the method further comprises dissociating the host molecule from the surface of the substrate. In some such embodiments, the dissociation is achieved by adding a molecule of greater affinity to the host molecule than the guest moiety of the functionalized silane. In some such embodiments, the dissociation is achieved by adding a molecule of greater affinity to the hydrophobic portion of the host molecule than the hydrophobic moiety of the functionalized silane. In some such embodiments, said molecule of greater affinity to the hydrophobic portion of the host molecule is 1,8-octanediol.

In some embodiments of the methods described herein, the method further comprises a washing step to recycle the substrate.

In any of the embodiments described herein, the guest moiety of the functionalized silane can comprise aryl, heteroaryl, heterocyclyl, cycloalkyl, cycloalkenyl, cycloalkynyl or adamantyl, or optionally substituted variants thereof. In some such embodiments, the hydrophobic moiety of the functionalized silane is substituted with one or more fluoro groups. In some such embodiments, the guest moiety comprises optionally substituted aryl. In some such embodiments, the guest moiety is optionally substituted aryl. In some other embodiments, the guest moiety comprises optionally substituted cycloalkenyl. In some other embodiments, the guest moiety is optionally substituted cycloalkenyl. In some such embodiments, the cycloalkenyl is norbornene.

In any of the embodiments described herein, the functionalized silane can be applied onto the surface of the substrate by chemical vapor deposition (CVD). In some other embodiments, the silane or silane derivative can be applied onto the first surface by chemical vapor deposition using a Yield Engineering Systems (YES) brand oven (Livermore, Calif.). In still some other embodiments, the silane or silane derivative can be applied in a liquid state via dip, spin or spray coating as needed.

In any of the embodiments described herein, the substrate can comprise a material selected from glass, silica, quartz, plastic, metal, metal oxide, patterned or not or combinations thereof. In one embodiment, the surface of the substrate comprises glass. In some embodiments, the surface of the substrate can comprise both functionalized silane coated regions and inert regions. In some embodiments, the inert regions are selected from glass regions, metal regions, mask regions and interstitial regions, or combinations thereof. In one embodiment, the inert regions comprise glass.

DETAILED DESCRIPTION

Figure 1:
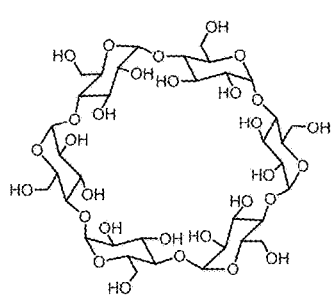
FIG. 1 shows alpha, beta and gamma-cyclodextrin and the corresponding cone shaped structure mimic.
Figure 1:
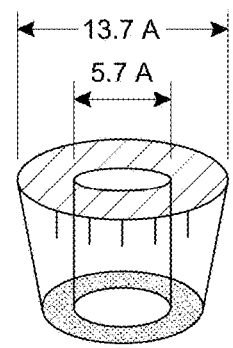
Figure 1:
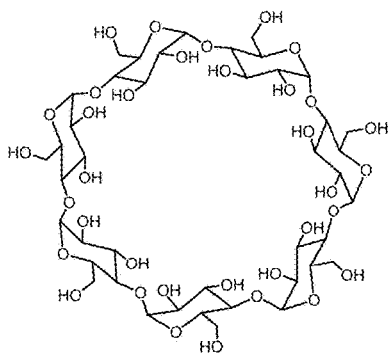
Figure 1:
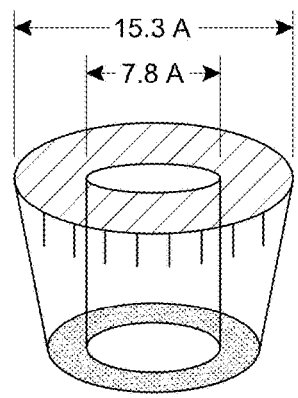
Figure 1:
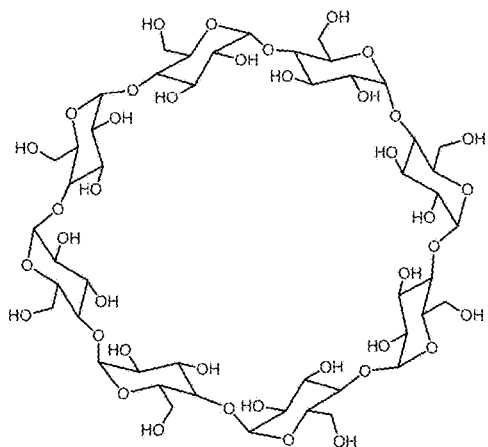
Figure 1:
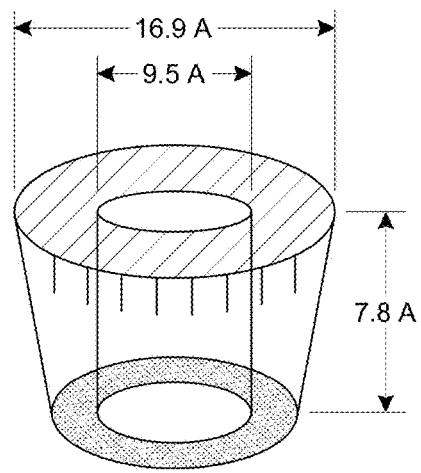

The present application relates to processes to immobilize or anchor a biological molecule of interest, such as DNA, on a surface using a reversible interaction, for example a non-covalent interaction. In one embodiment, this process is used as part of a sequencing by synthesis (SBS) reaction on a system such as the HiSeq®, MiSeq® or NextSeq® systems from Illumina (San Diego, Calif.). In these reactions, a set of amplification primers are typically bound to a glass surface. A set of target DNA molecules to be sequenced is hybridized to the bound primers and then amplified by a bridge amplification process. The sequencing reactions are carried out, and in embodiments of the invention, the amplification primers (and amplicons including primers extended during amplification steps to include copies of the target DNA) are then unbound from the glass surface so that the surface is reusable in future sequencing reactions. Thus, one or more of the steps of attaching amplification primers to the glass surface, hybridizing target DNA molecules to the primers, bridge amplification, sequencing the target DNA, and removing amplification primers and amplicons can be repeated. One or more repetition can be carried out.

In one embodiment, host/guest or inclusion complexes chemistry is used to attach the SBS primers onto the glass surface. The primers can be the P5 or P7 primers in one embodiment, as detailed below. The P5 and P7 primers are used on the surface of commercial flow cells sold by Illumina Inc. for sequencing on the HiSeq®, MiSeq®, NextSeq® and Genome Analyzer® platforms. The primer sequences are described in US Pat. Pub. No. 2011/0059865 A1, which is incorporated herein by reference in its entirety.

The P5 and P7 primer sequences comprise the following:

```
Paired end set:              SEQ ID NO: 1
P5: paired end 5'→ 3'
AATGATACGGCGACCACCGAGAUCTACAC P7: paired end 5'→ 3'        SEQ ID NO: 2
CAAGCAGAAGACGGCATACGAG*AT Single read set:             SEQ ID NO: 3
P5: single read: 5'→ 3'
AATGATACGGCGACCACCGA P7: single read 5'→ 3'       SEQ ID NO: 4
CAAGCAGAAGACGGCATACGA
```

In this embodiment, the goal is to be able to regenerate the flow cell surface while leaving the functionalized silane as intact as possible. In some embodiments, cyclodextrin is used as a host molecule to form a non-covalent host/guest complex with the functionalized silane. Cyclodextrin can be readily de-complexed from the silane moiety by shifting the thermodynamic equilibrium, for example. This can be achieved by using a guest with a higher affinity or binding constant for the internal cavity of cyclodextrin and flow it at a larger concentration. In some embodiments, 1,8-octanediol is chosen as a guest with a very strong affinity for β-cyclodextrin. Other guest compounds may also be used. Wickstrom et al. has reported the semi-empirical calculation of fifty-seven different guest molecules for β-cyclodextrin and their relative binding affinity, including aliphatic alcohols or diols (such as, 2-propanol, 2-butanol, cyclobutanol, 3-bromo-1-propanol, cyclohexanol, and R-1-phenyl-1,2-ethanediol); aliphatic or aralkyl protonated amines (such as 2-methoxyphenethylammonium, 3-4-dihydroxyphenethylammonium); phenols (such as Resorcinol); esters (such as R-1-phenyl-1,2-ethanediol); amides (such as delta-valerolactam); large and nominally rigid guests and strong binders (such as cycloheptanol and cyclooctanol); nabumetone and naproxen. See Wickstrom et al, "Large Scale Affinity Calculations of Cyclodextrin Host-Guest Complexes: Understanding the Role of Reorganization in the Molecular Recognition Process," *J. Chem. Theory Comput.* 2013, 9, 3136-3150.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:

Ac Acetyl
$Ac_2O$ Acetic anhydride
APTS aminopropyl silane
APTES (3-aminopropyl)triethoxysilane
APTMS (3-aminopropyl)trimethoxysilane
aq. Aqueous
Azapa N-(5-azidoacetamidylpentyl)acrylamide
BCN Bicyclo[6.1.0]non-4-yne
Bn Benzyl
Brapa or BRAPA N-(5-bromoacetamidylpentyl)acrylamide
Bz Benzoyl
BOC or Boc tert-Butoxycarbonyl
Bu n-Butyl
cat. Catalytic
CVD Chemical vapor deposition
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
DBU 1,8-Diazabicyclo[5.4.0]undec-7-ene
DCM Methylene chloride
DIEA Diisopropylethylamine
DIPEA Diisopropylethylamine
DMF N,N'-Dimethylformamide
DMSO Dimethylsulfoxide
DPPA Diphenylphosphoryl azide
Et Ethyl
EtOAc Ethyl acetate
g Gram(s)
GPC Gel permeation chromatography
h or hr Hour(s)
iPr Isopropyl
KPi 10 mM potassium phosphate buffer at pH 7.0
KPS Potassium persulfate
IPA Isopropyl Alcohol
LCMS Liquid chromatography-mass spectrometry
LDA Lithium diisopropylamide
m or min Minute(s)
MeOH Methanol
MeCN Acetonitrile
mL Milliliter(s)

NaN₃ Sodium Azide
NHS N-hydroxysuccinimide
NHS-AA Acrylic acid N-hydroxysuccinimide ester
PAZAM poly(N-(5-azidoacetamidylpentyl)acrylamide-co-acrylamide) of any acrylamide to Azapa ratio
PG Protecting group
Ph Phenyl
ppt Precipitate
rt Room temperature
SBS Sequencing-by-Synthesis
SFA Silane free acrylamide
Sulfo-HSAB or SHSAB N-Hydroxysulfosuccinimidyl-4-azidobenoate
TEA Triethylamine
TEMPO (2,2,6,6-Tetramethylpiperidin-1-yl)oxyl
Tert, t tertiary
TFA Trifluoroacetic acid
THF Tetrahydrofuran
YES Yield Engineering Systems
μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the present application to distinguish beads in a liquid array, for example, using a microfluidic device, such as a fluorescent activated cell sorter (FACS), are described, for example, in U.S. Pat. No. 6,524,793. Further examples of arrays that can be used in the application include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment, for example, physical adsorption.

As used herein, the term "reversible interaction" refers to an association of molecules where such association can be reversed as contrasted to irreversible association. For example, the non-covalent interaction between a host and a guest can be reversed by the intervention of a molecule of greater affinity to the host. Other non-limiting examples involves the use reversible cross-linking agents such as formaldehyde, imine bond formation (see Stoddart in *Chem. Soc. Rev.*, 2012, 41, pp. 2003-2024; *Chem. Soc. Rev.* 2007, 36(11), pp. 1705-1723), metalo-directed imine bond formation (see Nitschke in *Acc. Chem. Res.*, 2007, 40 (2), pp. 103-112), disulphide bonds (see Black, et al in *Chem. Soc. Rev.*, 2014, 43, pp. 1861-1872), boronic acid exchange (see Wilson, et al in *Chem. Soc. Rev.*, 2014, 43, pp. 1948-1962), hydrogen bonding (see Seto, et al in *J. Am. Chem. Soc.*, 1993, 115 (4), pp. 1321-1329), π-stacking (see Schenning, et al in *Chem. Commun.* 2005, 14; (26):3245-58). In some other examples, the association of the molecules may be thermally reversible. See, e.g., Liu et al., *Macromolecular Chemistry and Physics*, 2007, 208(2), pp. 224-232.

As used herein, non-covalent interaction differs from a covalent bond in that it does not involve the sharing of electrons, but rather involves more dispersed variations of electromagnetic interactions between molecules or within a molecule. Non-covalent interactions can be generally classified into four categories, electrostatic, π-effects, van der Waals forces, and hydrophobic effects. Non-limiting examples of electrostatic interactions include ionic interactions, hydrogen bonding (a specific type of dipole-dipole interaction), halogen bonding, etc. Van der Walls forces are a subset of electrostatic interaction involving permanent or induced dipoles or multipoles. π-effects can be broken down into numerous categories, including (but not limited to) π-π interactions, cation-π & anion-π interactions, and polar-π interactions. In general, π-effects are associated with the interactions of molecules with the π-orbitals of a molecular system, such as benzene. The hydrophobic effect is the tendency of nonpolar substances to aggregate in aqueous solution and exclude water molecules. Non-covalent interactions can be both intermolecular and intramolecular.

As used herein, the term "percent surface remaining" refer to the intensity measured using a TET QC to stain surface primers, such as the P5 and P7 primers. The P5 and P7 primers can be used on the surface of commercial flow cells sold by Illumina Inc. for sequencing on the HiSeq®, MiSeq®, Genome Analyzer® and NextSeq® platforms. The primer sequences are described in U.S. Pat. Pub. No. 2011/0059865 A1, which is incorporated herein by reference. TET is a dye labeled oligonucleotide having complimentary sequence to the P5/P7 primers. TET can be hybridized to the P5/P7 primers on a surface; the excess TET can be washed away, and the attached dye concentration can be measured by fluorescence detection using a scanning instrument such as a Typhoon Scanner (General Electric).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, CH₃—, CH₃CH₂—, CH₃CH₂CH₂—, (CH₃)₂CH—, CH₃CH₂CH₂CH₂—, CH₃CH₂CH(CH₃)— and (CH₃)₃C—.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "arylene" refers to an aromatic ring or ring system containing only carbon and hydrogen that is attached to the rest of the molecule via two points of attachment.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

As used herein, "heteroarylene" refers to an aromatic ring or ring system containing one or more heteroatoms in the ring backbone that is attached to the rest of the molecule via two points of attachment.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne.

As used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "heterocyclylene" means a non-aromatic cyclic ring or ring system containing at least one heteroatom that is attached to the rest of the molecule via two points of attachment.

As used herein, an "amino" group refers to a "—$NR_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —$NH_2$).

The term "hydrazone" or "hydrazonyl" as used herein refers to a

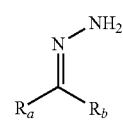

group.

The term "epoxy" as used herein refers to

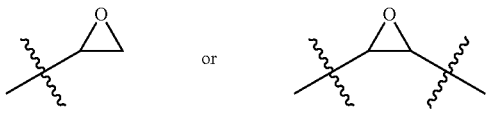

The term "glycidyl ether" as used herein refers to

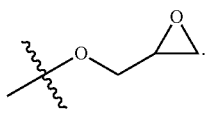 [SMILES: *OCC1CO1]

The term "carboxylic acid" or "carboxyl" as used herein refers to —C(O)OH.

As used herein, the term "tetrazine" or "tetrazinyl" refers to six-membered heteroaryl group comprising four nitrogen atoms. Tetrazine can be optionally substituted.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present at the 2' position in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but lacks any phosphate moieties at the 5' position. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

As used herein, the term "polynucleotide" refers to nucleic acids in general, including DNA (e.g. genomic DNA cDNA), RNA (e.g. mRNA), synthetic oligonucleotides and synthetic nucleic acid analogs. Polynucleotides may include natural or non-natural bases, or combinations thereof and natural or non-natural backbone linkages, e.g. phosphorothioates, PNA or 2'-O-methyl-RNA, or combinations thereof.

As used herein, the term "primer" is defined as a single strand DNA (ssDNA) molecule with a free 3' OH group and a modification at the 5' terminus to allow the coupling reactions. The primer length can be any number of bases long and can include a variety of non-natural nucleotides. "BCN primer" or "BCN modified primer" refers to a primer comprising covalently attached bicyclo[6.1.0]non-4-yne at the 5' terminus.

As used herein, the term "silane" refers to an organic or inorganic compound containing one or more silicon atoms. Non-limiting example of an inorganic silane compound is $SiH_4$, or halogenated $SiH_4$ where hydrogen is replaced by one or more halogen atoms. Non-limiting example of an organic silane compound is $X-R^C-Si(OR^D)_3$, wherein X is a non-hydrolyzable organic group, such as amino, vinyl, epoxy, methacrylate, sulfur, alkyl, alkenyl, alkynyl; $R^C$ is a spacer, for example $-(CH_2)_n-$, wherein n is 0 to 1000; $R^D$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the term "silane" can comprise mixtures of different silane compounds.

As used herein, the term "YES method" refers to the chemical vapor deposition tool provided by Yield Engineering Systems ("YES") (Livermore, Calif.) with a chemical vapor deposition process developed by Illumina, Inc. It includes three different vapor deposition systems. The automated YES-VertaCoat silane vapor system is designed for volume production with a flexible wafer handling module that can accommodate 200 or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., $-CF_3$), halo($C_1$-$C_6$)alkoxy (e.g., $-OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $-CH_2-$, —CH$_2$CH$_2$—, —CH$_2$CH(CH$_3$)CH$_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated.

Where the compounds disclosed herein have at least one stereocenter, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures; the artisan recognizes that such structures may only represent a very small portion of a sample of such compound(s). Such compounds are considered within the scope of the structures depicted, though such resonance forms or tautomers are not represented herein.

Host Molecules

Some embodiments described herein relate to the use of a host molecule to form a host/guest inclusion complex through a non-covalent interaction. The host/guess chemistry describes complexes that are composed of two or more molecules or ions that are held together in unique structural relationship by form other than covalent bonding. There is a thermodynamic equilibrium between the unbound state, in which host and guest are separate from each other, and the bound state, in which there is a structurally defined host-guest complex. In some embodiments, the host molecule comprises a hydrophilic portion and a hydrophobic portion.

Common host molecules are cyclodextrins, calixarenes, pillararenes, cucurbiturils, porphyrins, metallacrowns, crown ethers, zeolites, cyclotriveratrylenes, cryptophanes, carcerands, and foldamers. In some embodiments, the host molecule is optionally substituted cyclodextrin or derivatives thereof.

The host molecule may comprise one or more functional groups for reacting with a biological molecule of interest to form a covalent bond. In some embodiments, the biological molecule is an oligonucleotide, such as a primer, or a longer molecule, such as a polynucleotide. In some embodiments, the host molecule comprises one or more azido groups that react with alkyne or BCN functionalized primers.

Cyclodextrin

As used herein, the term "cyclodextrin" includes any of the known cyclodextrins, such as optionally substituted cyclodextrins containing from six to twelve glucopyranose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units. Cyclodextrins can be topologically represented as toroids (i.e., donut or cone-shaped rings) with the larger and the smaller openings of the toroid exposing to the secondary and primary hydroxyl groups respectively. The specific coupling and conformation of the glucose units give the cyclodextrins rigid, conical molecular structures with hollow interiors of specific volumes. Because of this arrangement, a "lining" of the internal cavity of cyclodextrin is formed by hydrogen atoms and glycosidic bridging oxygen atoms; therefore, this surface is fairly hydrophobic and thus able to host other hydrophobic molecules. In contrast, the exterior is sufficiently hydrophilic to impart cyclodextrins (or their complexes) water solubility. FIG. 1 illustrates the structure of alpha-cyclodextrin, beta-cyclodextrin, gamma-cyclodextrin and their corresponding toroidal structures.

The ability of a cyclodextrin to form an inclusion complex with a guest molecule is a function of two factors. The first is steric and depends on the relative size of the cyclodextrin as compared with the size of the guest molecule or certain key functional groups within the guest. If the guest is the wrong size, it will not fit properly into the cyclodextrin cavity. The second factor is the thermodynamic interactions between the different components of the system (cyclodextrin, guest, solvent). The driving force for the encapsulation is of hydrophilic/hydrophobic nature, the guest minimizes its interaction with polar solvent taking shelter inside the lipophilic cavity of the cyclodextrin.

The potential guest molecule for molecular encapsulation within a cyclodextrin is quite varied and includes compounds such as straight or branched chain aliphatics, aldehydes, ketones, alcohols, organic acids, fatty acids, aromatics, and polar compounds such as halogens, oxyacids and amines.

Cyclodextrin may be optionally substituted with one or more substituents selected from $C_{1-6}$ alkyl, amino, $C_{1-6}$ haloalkyl, halogen, hydroxy, $C_{1-6}$ alkoxy, $C_{1-6}$ haloalkoxy, cyano, sulfonyl or oxo. The derivatives of cyclodextrin include molecules where some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —CH$_2$—CH(OH)—CH$_3$ or a —CH$_2$CH$_2$—OH group; branched cyclodextrins such as maltose-bonded cyclodextrins; cationic cyclodextrins such as those containing 2-hydroxy-3-(dimethylamino)propyl ether, wherein R is —CH$_2$—CH(OH)—CH$_2$—N(CH$_3$)$_2$; quaternary ammonium, e.g., 2-hydroxy-3-(trimethylammonio)propyl ether chloride groups, wherein R is CH$_2$—CH(OH)—CH$_2$—N$^+$(CH$_3$)$_3$Cl; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins.

In some instance, cyclodextrin derivatives may include cyclodextrin based or cyclodextrin functionalized polymer or hydrogel materials.

The cyclodextrin or cyclodextrin derivatives described herein also may comprise one or more reactive functional groups that can form covalent bonding with a biological molecule of interest. In some embodiments, the cyclodextrin host molecule comprises one or more azido groups that can be used for reaction with one or more functionalized biological molecule, such as primers.

Biological Molecules

As used herein, non-limiting examples of biological molecules of interest include amino acids, peptides, nucleotides (e.g. deoxyribonucleotides or ribonucleotides in mono-, di- or tri-phosphate forms), oligonucleotides, polynucleotides, proteins, sugars, polysaccharides or combinations thereof. The biological molecule may comprise one or more functional groups that are capable of forming covalent bonding with the host molecule. In some embodiments, the biological molecule comprises a functionalized oligonucleotide or primer that can react with one or more functional groups of the host molecule. In some embodiments, the biological molecule is a functionalized oligonucleotide or primer that can react with one or more functional groups of the host molecule. In some embodiments, the host molecule is cyclodextrin or optionally substituted variants and derivatives thereof. In some such embodiments, the biological molecule is attached to the hydrophilic portion of the cyclodextrin, i.e., the exterior wall of the toroidal structure of cyclodextrin.

Non-limiting examples of functionalized oligonucleotides or primers include alkyne or bicycle[6.1.0]nonyne ("BCN") functionalized oligonucleotides, or any other functionalized oligonucleotide comprising a strained ring system that is capable of undergoing strain-promoted azide-alkyne cycloaddition, such as azide cyclooctyne reaction, as understood by one of ordinary skill in the art. Additional information on strain-promoted azide-alkene or azide-alkyne cycloaddition can be found in U.S. Ser. No. 14/316,478, which is hereby incorporated by reference in its entirety.

In some embodiments, the functionalized oligonucleotide is pre-conjugated to a polymer and the polymer comprises one or more functional groups that can form covalent bonding with the host molecule. Non-limiting examples of the polymers that can be used in embodiments described herein can be found in U.S. Ser. No. 13/784,368 and U.S. Pat. Pub. No. 2011/0059865, which are hereby incorporated by references in their entireties.

In some embodiments, the poly(N-(5-azidoacetamidylpentyl)acrylamide-co-acrylamide) (PAZAM) polymer described herein is represented by Formula (Ia) or (Ib):

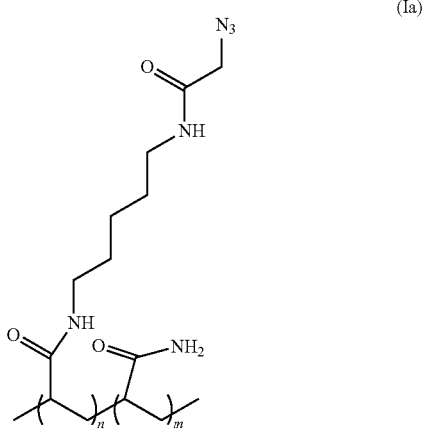

(Ia)

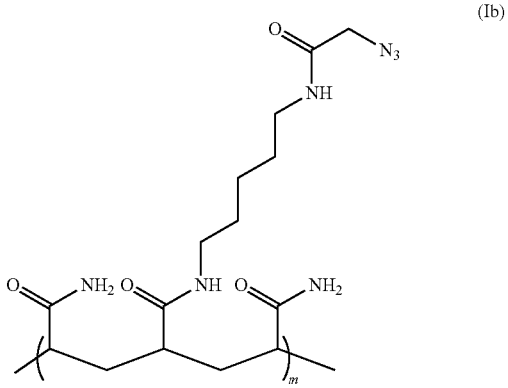

(Ib)

wherein n is an integer in the range of 1-20,000, and m is an integer in the range of 1-100,000. Non-limiting examples of oligonucleotide or primer that can react with PAZAM include alkyne or bicycle[6.1.0]nonyne ("BCN") functionalized oligonucleotide, or any other functionalized oligonucleotide comprising a strained ring system that is capable of undergoing strain-promoted azide-alkyne cycloaddition. In some such embodiments, the host molecule comprises one or more alkyne groups that can react with the azido groups of PAZAM.

Other pre-conjugated oligonucleotides may comprise one or more functional groups such as amino, azido, carboxylic acid, acid anhydride, tetrazine, epoxy, glycidyl ether, vinyl, acryloyl, alkenyl, cycloalkenyl, heterocycloalkenyl, alkynyl, cycloalkynyl, heterocycloalkynyl, nitrene, aldehyde, hydrazinyl, or maleimide groups that can react with one or more functional groups of the host molecule. In one embodiment, the pre-conjugated oligonucleotide may comprise one or more tetrazine groups that react with one or more strained cycloalkene groups (such as trans-cyclooctene) of the host molecule. In another embodiment, the pre-conjugated oligonucleotide may comprise one or more epoxy, carboxylic acid, acid anhydride or glycidyl ether group that reacts with one or more amino groups of the host molecule. In still another embodiment, the pre-conjugated oligonucleotide may comprise one or more amino groups that react with one or more epoxy or glycidyl ether groups of the host molecule.

Functionalized Silane

Some embodiments disclosed herein relate to functionalized silane comprising a moiety that can form host-guest complex with the host molecule. In some embodiments, the functionalized silane comprises a hydrophobic moiety. In some embodiments, the hydrophobic moiety comprises aryl, heteroaryl, heterocyclyl, cycloalkyl, cycloalkenyl, cycloalkynyl, or adamantyl, or optionally substituted variants. In some such embodiments, aryl can be phenyl. In some of these embodiments, each heteroaryl, heterocyclyl, cycloalkyl, cycloalkenyl, or cycloalkynyl group can be selected from a 5, 6, 7, 8, 9 or 10 membered ring system.

In some embodiments, cycloalkene is selected from norbornene or a norbornene derivative, such as a (hetero) norbornene where one or more carbon atoms in the norbornene molecule in replaced by one or more heteroatoms. Non-limiting examples of other cycloalkenes include optionally substituted cyclooctene, optionally substituted cyclopentene, optionally substituted cyclohexene, optionally substituted cycloheptene, optionally substituted cyclononene, optionally substituted bicyclo[3.3.1]non-1-ene, optionally substituted bicyclo[4.3.1]dec-1(9)-ene, optionally substituted bicyclo[4.2.1]non-1(8)-ene, and optionally substituted bicyclo[4.2.1]-non-1-ene.

In some embodiments, the cycloalkyne is cyclooctyne or a cyclooctyne derivative. Non-limiting examples of a cyclooctyne derivative include the following structures:

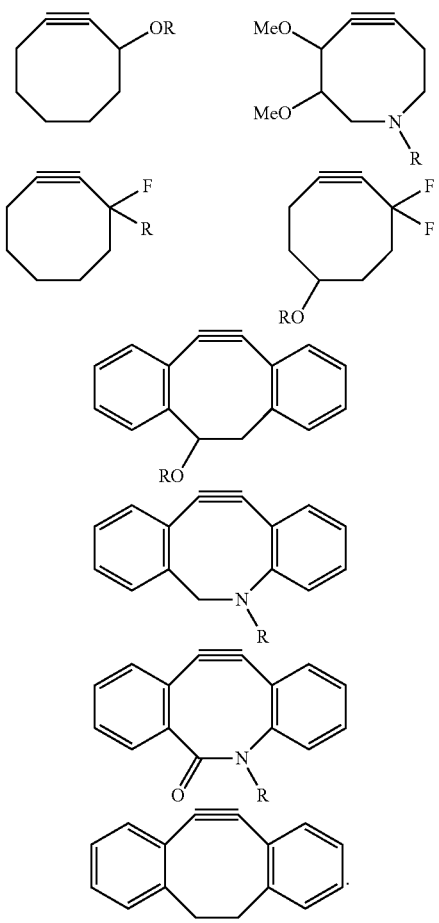

In some other embodiments, the hydrophobic moiety of the functionalized silane comprises cycloalkyl, such as cyclohexyl, or optionally substituted variants thereof.

In some other embodiments, the hydrophobic moiety comprises an aliphatic group, such as straight chain or branched alkyl.

In any embodiments described herein, the hydrophobic moiety may be optionally substituted with one or more substituents selected from $C_{1-6}$ alkyl, amino, $C_{1-6}$ haloalkyl, halogen, hydroxy, carboxy, $C_{1-6}$ alkoxy, $C_{1-6}$ haloalkoxy, cyano, sulfonyl, thiol, or oxo. In some such embodiments, the hydrophobic moiety may be optionally substituted with hydroxy.

Substrates

In some embodiments, substrates used in the present application include silica-based substrates, such as glass, fused silica and other silica-containing materials. In some embodiments, silica-based substrates can also be silicon, silicon dioxide, silicon nitride, silicone hydrides. In some embodiments, substrates used in the present application include plastic materials such as polyethylene, polystyrene, poly(vinyl chloride), polypropylene, nylons, polyesters, polycarbonates and poly(methyl methacrylate). Preferred plastics material are poly(methyl methacrylate), polystyrene and cyclic olefin polymer substrates. In some embodiments, the substrate is a silica-based material or plastic material. In one embodiment, the substrate has at least one surface comprising glass.

In some other embodiments, the substrates can be a metal, such as gold, or a metal oxide, such as tantalum oxide.

Acrylamide, enone, or acrylate may also be utilized as a substrate material. Other substrate materials can include, but are not limited to gallium aresnide, indium phosphide, aluminum, ceramics, polyimide, quartz, resins, polymers and copolymers. The foregoing lists are intended to be illustrative of, but not limited to the present application.

Substrates can comprise a single material or a plurality of different materials. Substrates can be composites or laminates. Substrate can be flat, round, textured and patterned. Patterns can be formed, for example, by metal pads that form features on non-metallic surfaces, for example, as described in U.S. Pat. No. 8,778,849, which is incorporated herein by reference. Another useful patterned surface is one having well features formed on a surface, for example, as described in U.S. Ser. No. 13/787,396, US Pat. App. Pub. No. 2011/0172118 A1 or U.S. Pat. No. 7,622,294, each of which is incorporated herein by reference. For embodiments that use a patterned substrate, a gel can be selectively attached to the pattern features (e.g. gel can be attached to metal pads or gel can be attached to the interior of wells) or alternatively the gel can be uniformly attached across both the pattern features and the interstitial regions.

In some embodiments, the surface of the substrate comprises both functional molecule-coated regions and inert regions with no coatings. In some such embodiments, the functionalized molecule coatings are hydrogel or polymer coatings. The functional molecule-coated regions can comprise reactive sites, and thus, can be used to attach molecules through chemical bonding or other molecular interactions. In some embodiments, the functional molecule-coated regions (e.g. reactive features, pads, beads or wells) and the inert regions (referred to as interstitial regions) can alternate so as to form a pattern or a grid. Such patterns can be in one or two dimensions. In some embodiments, the inert regions can be selected from glass regions, metal regions, mask regions or interstitial regions, or combinations thereof. Alternatively these materials can form reactive regions. Inertness or reactivity will depend on the chemistry and processes used on the substrate. In one embodiment, the surface comprises glass regions. In another embodiment, the surface comprises metal regions. In still another embodiment, the surface comprises mask regions. In some embodiments of the compositions described herein, the substrate can be a bead. Non-limiting exemplary substrate materials that can be coated with a polymer of the present disclosure or that can otherwise be used in a composition or method set forth herein are described in U.S. Pat. Nos. 8,778,848 and 8,778,849, each of which is incorporated herein by reference.

In some embodiments, a substrate described herein forms at least part of a flow cell, or is located in a flow cell. In some such embodiments, the flow cells further comprise polynucleotides attached to the surface of the substrate via the functional molecule coating, for example, a polymer coating. In some embodiments, the polynucleotides are present in the flow cells in polynucleotide clusters, wherein the polynucleotides of the polynucleotide clusters are attached to a surface of the flow cell via the polymer coating. In such embodiments, the surface of the flow cell body to which the polynucleotides are attached is considered the substrate. In other embodiments, a separate substrate having a polymer coated surface is inserted into the body of the flow cell. In some embodiments, the flow cell is a flow chamber that is divided into a plurality of lanes or a plurality of sectors, wherein one or more of the plurality of lanes or plurality of sectors comprises a surface that is coated with a covalently attached polymer coating described herein. In some embodiments of the flow cells described herein, the attached polynucleotides within a single polynucleotide cluster have the same or similar nucleotide sequence. In some embodiments of the flow cells described herein, the attached polynucleotides of different polynucleotide clusters have different or nonsimilar nucleotide sequences. Exemplary flow cells and substrates for manufacture of flow cells that can be used in method or composition set forth herein include, but are not limited to, those commercially available from Illumina, Inc. (San Diego, Calif.) or described in US 2010/0111768 A1 or US 2012/0270305, each of which is incorporated herein by reference in its entirety.

Sequencing Application

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a polymer coating. In PCR embodiments, one or both of the primers used for amplification can be attached to a polymer coating. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference in its entirety.

PCR amplification can also be carried out with one of the amplification primers attached to a polymer coating and the second primer in solution. An exemplary format that uses a combination of one attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to substrate or solid supports as set forth in the ePCR references and can instead be attached to a polymer coating as set forth herein.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a polymer coating.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. No. 5,455,166; U.S. Pat. No. 5,130,238; and U.S. Pat. No. 6,214,587, each of which is incorporated herein by reference. Primers used for MDA can be in solution or attached to a polymer coating.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a polymer coating. In this example, amplicons produced after the combined RCA and MDA steps will be attached to the polymer coating.

In some embodiments, the functionalized hydrogel or polymer-coated substrate described herein can be used for determining a nucleotide sequence of a polynucleotide. In such embodiments, the method can comprise the steps of (a) contacting a polynucleotide polymerase with polynucleotide clusters attached to a surface of a substrate via any one of the polymer or hydrogel coatings described herein; (b) providing nucleotides to the polymer-coated surface of the substrate such that a detectable signal is generated when one or more nucleotides are utilized by the polynucleotide polymerase; (c) detecting signals at one or more polynucleotide clusters; and (d) repeating steps (b) and (c), thereby determining a nucleotide sequence of a polynucleotide present at the one or more polynucleotide clusters.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate via any one of the polymer coatings described herein. In such process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide. Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference in its entirety.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. No. 6,210,891; U.S. Pat. No. 6,258,568 and U.S. Pat. No. 6,274,320, each of which is incorporated herein by reference in its entirety). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WO 12/058096 A1, US 2005/0191698 A1, U.S. Pat. No. 7,595,883, and U.S. Pat. No. 7,244,559, each of which is incorporated herein by reference in its entirety.

Sequencing-by-ligation reactions are also useful including, for example, those described in Shendure et al. *Science* 309:1728-1732 (2005); U.S. Pat. No. 5,599,675; and U.S. Pat. No. 5,750,341, each of which is incorporated herein by reference in its entirety. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference in its entirety. In both sequencing-by-ligation and sequencing-by-hybridization procedures, nucleic acids that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. Science 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in its entirety.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety.

In some embodiments of the above-described method which employ a flow cell, only a single type of nucleotide is present in the flow cell during a single flow step. In such embodiments, the nucleotide can be selected from the group consisting of dATP, dCTP, dGTP, dTTP and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises and optical signal. In other embodiments, the detectable signal comprises a non-optical signal. In such embodiments, the non-optical signal comprises a change in pH at or near one or more of the polynucleotide templates.

EXAMPLES

Additional embodiments are disclosed in further detail in the following examples, which are not in any way intended to limit the scope of the claims.

Example 1

Figure 2:
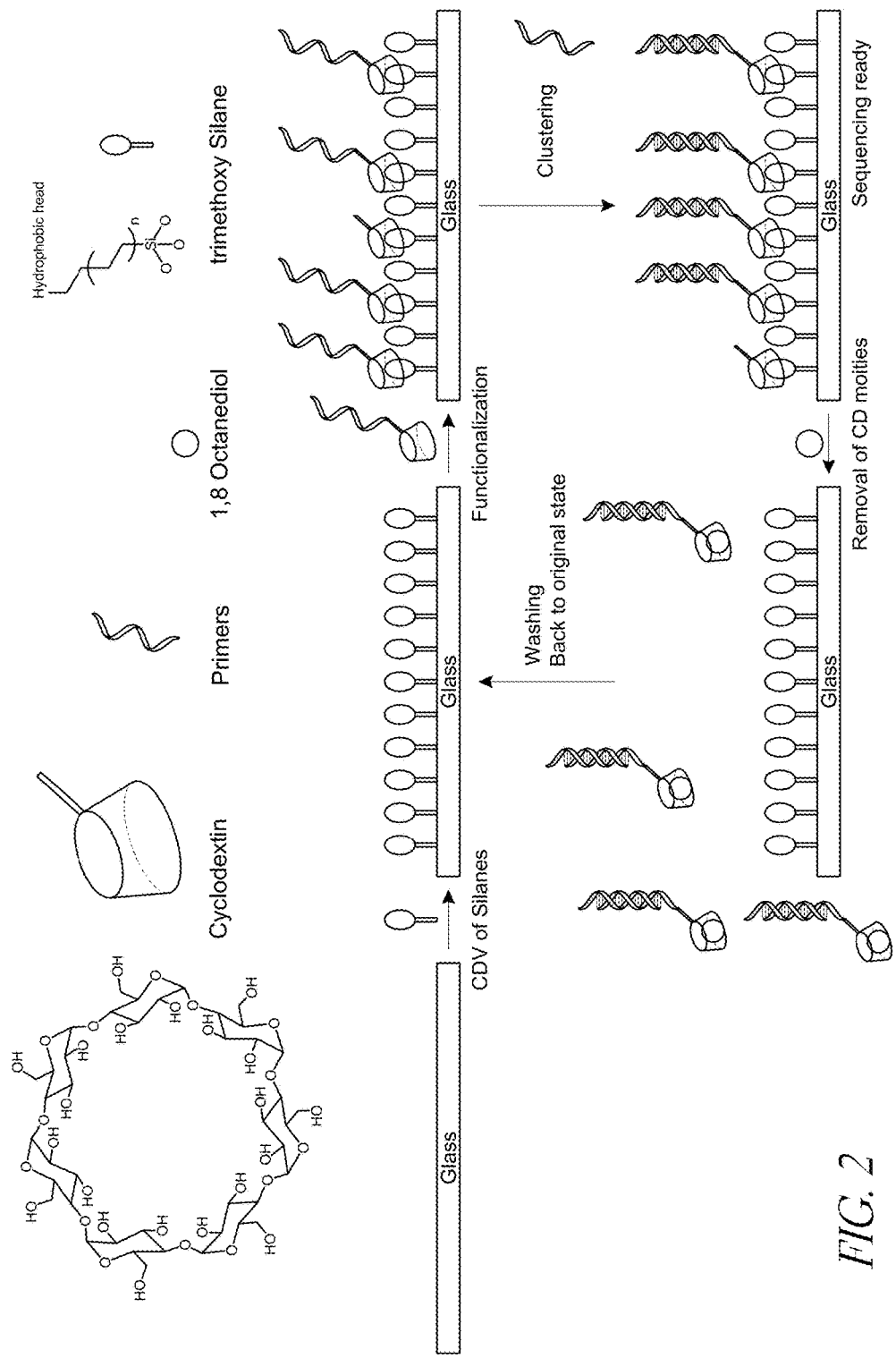
FIG. 2 shows the work flow process of reversibly attaching an oligonucleotide to a silane functionalized surface.

FIG. 2 illustrates an embodiment of a method of reversibly attaching a biological molecule to a silane functionalized surface. A substrate comprising a glass surface was first treated with a functionalized silane comprising a hydrophobic portion by chemical vapor deposition (CVD). Cyclodextrin was used as a host molecule and functionalized primers were grafted to the cyclodextrin by reacting with one or more azido groups of the cyclodextrin. Then, the silanized surface was contacted with cyclodextrin bonded primers such that the hydrophobic head of the silane formed a host-guest inclusion complex with the inner cavity of the cyclodextrin through reversible interaction. As a result, the primers were immobilized to the surface of the substrate. After standard clustering and sequencing processes, the cyclodextrin was dissociated from the surface by adding 1,8-octanediol, a molecule of greater affinity to the inner cavity of the cyclodextrin than the hydrophobic head of the functionalized silane and the silanized glass surface was washed and regenerated. This process is discussed in more detail below in the following example.

Example 2

In a first experiment, a fluorescein isothiocyanate (FITC) functionalized cyclodextrin was reacted with a norbornene silane functionalized surface for 30 mins at 50° C., followed by rinsing with a different solvent. Methods for preparing such a norbornene silane functionalized surface is described in detail in U.S. patent application Ser. No. 14/316,478, which is hereby incorporated by reference in its entirety.

In this experiment, NextSeq® and HiSeq® flow cells were silanized using a standard norbornene silane, [(5-bicyclo[2.2.1]hept-2-enyl)ethyl]trimethoxysilane. The norbornene moiety is lipophilic and can act as a guest for cyclodextrin. According to a molecular mechanic prediction obtained from the literature, only the bridging methylene from the norbornene would fit into the inner cavity of cyclodextrin (binding free energy around −2 kcal/mol). Other possible guests with more stable host-guest complexes could also be used, for example, guests comprising a planar aromatic ring, such as phenyl or naphthyl group are better fit for β-cyclodextrin. See, Wickstrom et al., "Large Scale Affinity Calculations of Cyclodextrin Host-Guest Complexes: Understanding the Role of Reorganization in the Molecular Recognition Process," *J. Chem. Theory Comput.*, 2013, 9 (7), pp. 3136-3150.

After the flow cell was silanized, it was incubated in the presence of cyclodextrin that had been previously grafted with a mixture of P5 and P7 oligos. The pre-grafted cyclodextrin was prepared by reacting the azido functionalized cyclodextrin with a mixture of alkyne terminated P5 and P7 oligos via copper-directed cycloaddition as shown in the scheme described below.

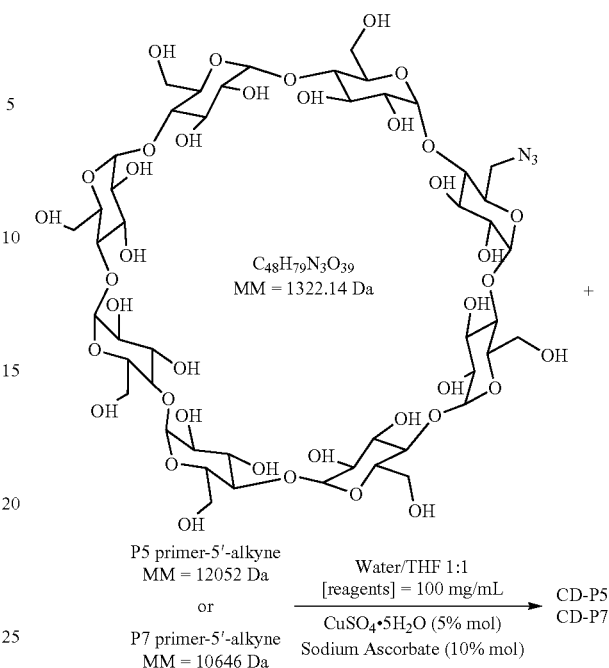

Alternatively, the primers can also be attached to the cyclodextrin after its anchorage to the silane functionalized surface. After incubation, the flow cell was washed and TET QC was performed on the surface. The results obtained for the HiSeq flow cell is discussed below.

Figure 3A:
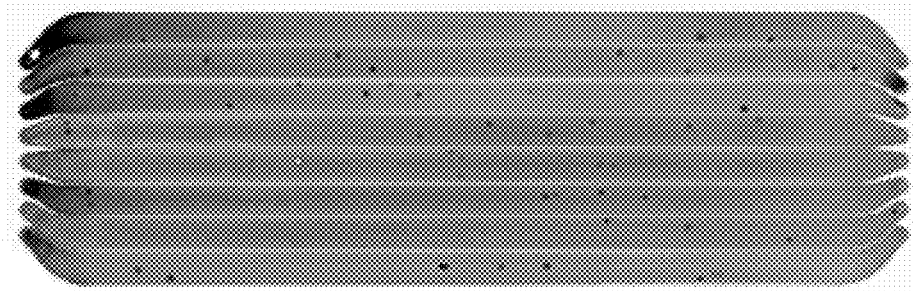
FIG. 3A shows a TET scan Typhoon image of a primer-functionalized cyclodextrin immobilized on a norbornene-silane derivative [(5-bicyclo[2.2.1]hept-2-enyl)ethyl]trimethoxysilane functionalized surface of a substrate.
Figure 3B:
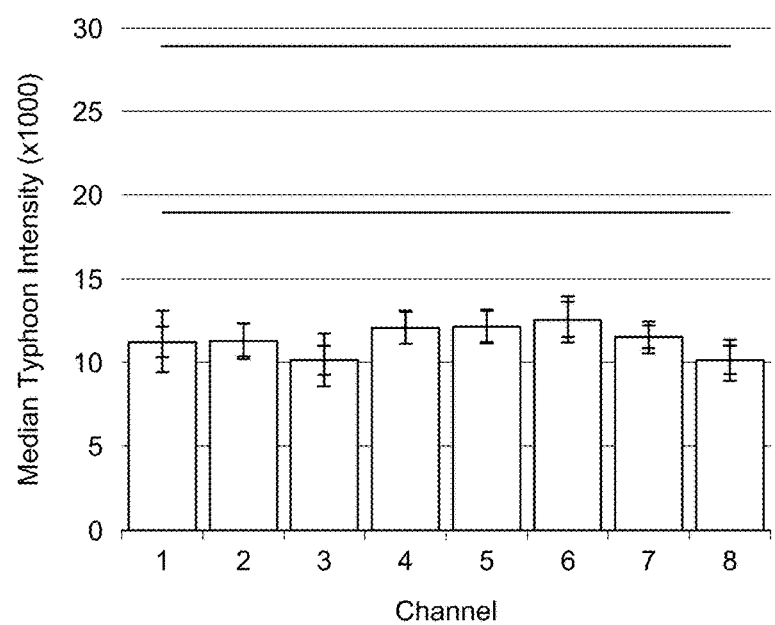
FIG. 3B shows the related chart of median Typhoon intensity of the cyclodextrin primer grafted surface.

The fluorescence count obtained was around 1000. In contrast, no signal was observed for experiments performed on a non-silanized flow cell, demonstrating that there is a molecular recognition between cyclodextrin and the surficial norbornene and this allow DNA in the form of primers to be immobilized on the surface. As demonstrated in FIG. 3A, the Typhoon image of the primer conjugated cyclodextrin polymer immobilized to a norbornene silane functionalized surface proves that cyclodextrin is attached to the surface. The median Typhoon intensity chart as shown in FIG. 3B suggests that cyclodextrin is not attached to the surface covalently.

Thus, it was discovered that it is possible to attached DNA to a glass surface through host-guest inclusion complex involving a hydrophobic silane and cyclodextrin. In addition, the small amount of inclusion complex thus formed on the surface was stable to the flow necessary for TET QC, washes and clustering.

This system can be further improved by using a different hydrophobic silane, or by tweaking the surface coverage of this silane or by selecting a different cyclodextrin or polymeric cyclodextrin (multiple cyclodextrin attached together to increase the size of the layer and its stability) in order to obtain the more stable inclusion complexes, or by finding the right condition for cyclodextrin anchoring on the surface.

What is claimed is:

1. A method for reversibly immobilizing a biological molecule to a surface of a substrate, comprising:
   providing a biological molecule covalently bonded to a host molecule, said host molecule comprises a hydrophilic portion and a hydrophobic portion, wherein the biological molecule comprises a primer oligonucleotide and wherein said host molecule comprises an optionally substituted cyclodextrin or a derivative thereof;
   providing a substrate having a surface comprising functionalized silane covalently attached thereto, wherein the functionalized silane comprises a guest moiety that can form a host-guest complex with the host molecule;
   contacting the biological molecule with the functionalized silane such that the biological molecule is immobilized to the surface through the host-guest reversible interaction between the functionalized silane and the host molecule; and
   generating a clustered array of polynucleotides from the primer oligonucleotide.

2. The method of claim 1, wherein the host-guest interaction is a non-covalent interaction between the guest moiety of the functionalized silane and the host molecule.

3. The method of claim 1, wherein the guest moiety of the functionalized silane comprises a hydrophobic moiety.

4. The method of claim 3, wherein the host-guest non-covalent interaction is between the hydrophobic moiety of the functionalized silane and the hydrophobic portion of the host molecule.

5. The method of claim 1, wherein the biological molecule is covalently bonded to the hydrophilic portion of the host molecule.

6. The method of claim 1, further comprising dissociating the host molecule from the surface of the substrate.

7. The method of claim 6, wherein the dissociation is achieved by adding a molecule of greater affinity to the host molecule than the guest moiety of the functionalized silane.

8. The method of claim 7, wherein the dissociation is achieved by adding a molecule of greater affinity to the hydrophobic portion of the host molecule than the hydrophobic moiety of the functionalized silane.

9. The method of claim 8, wherein said molecule of greater affinity to the hydrophobic portion of the host molecule is 1,8-octanediol.

10. The method of claim 1, wherein the host molecule is β-cyclodextrin.

11. The method of claim 1, further comprising a washing step to recycle the substrate.

12. The method of claim 1, wherein the guest moiety of the functionalized silane comprises aryl, heteroaryl, heterocyclyl, cycloalkyl, cycloalkenyl, or cycloalkynyl, or optionally substituted variants thereof with one or more functional groups capable of forming covalent bonding with a functionalized polymer or hydrogel coating for surface functionalization.

13. The method of claim 12, wherein the guest moiety comprises aryl.

14. The method of claim 12, wherein the guest moiety comprises cycloalkenyl.

15. The method of claim 14, wherein the cycloalkenyl is norbornene.

16. The method of claim 1, wherein the guest moiety is substituted with one or more fluoro groups.

17. A method for reversibly immobilizing a biological molecule to a surface of a substrate, comprising:
    providing a biological molecule covalently bonded to a host molecule, said host molecule comprises a hydrophilic portion and a hydrophobic portion;
    providing a substrate having a surface comprising functionalized silane covalently attached thereto, wherein the functionalized silane comprises a guest moiety that can form a host-guest complex with the host molecule;
    contacting the biological molecule with the functionalized silane such that the biological molecule is immobilized to the surface through the host-guest reversible interaction between the functionalized silane and the host molecule,
    wherein the guest moiety of the functionalized silane comprises norbornene.

18. The method of claim 17, wherein said host molecule comprises an optionally substituted cyclodextrin or a derivative thereof.

19. The method of claim 17, wherein the biological molecule comprises a primer oligonucleotide.

* * * * *